United States Patent [19]

Thompson

[11] Patent Number: 4,940,583

[45] Date of Patent: Jul. 10, 1990

[54] ANIMAL REPELLENT COMPOSITION AND METHOD

[75] Inventor: Ian A. Thompson, New South Wales, Australia

[73] Assignee: R & C Products Pty. Limited, Chatswood, Australia

[21] Appl. No.: 116,049

[22] Filed: Nov. 2, 1987

[51] Int. Cl.[5] .............................................. H01N 33/00
[52] U.S. Cl. .................................. 424/195.1; 424/10; 514/307
[58] Field of Search .................. 424/78, 143, 331, 333, 424/195.1, 196.1; 514/255, 460, 307

[56] References Cited

U.S. PATENT DOCUMENTS

| | | | |
|---|---|---|---|
| 3,069,314 | 12/1962 | Jenkins | 167/46 |
| 3,474,176 | 10/1969 | Freeman | 424/331 |
| 3,923,997 | 12/1975 | Meuly | 514/460 X |
| 4,010,196 | 3/1977 | Tsuk | 424/78 X |
| 4,058,626 | 11/1977 | Roth | 424/333 |
| 4,179,499 | 12/1979 | Christensen | 424/143 X |
| 4,320,112 | 3/1982 | Jones et al. | 424/19 |
| 4,451,452 | 5/1984 | Deibig et al. | 514/255 X |
| 4,479,889 | 10/1984 | DiPaola et al. | 252/365 |

FOREIGN PATENT DOCUMENTS

| | | |
|---|---|---|
| 2738002 | 4/1978 | Fed. Rep. of Germany . |
| 85/05009 | 11/1985 | PCT Int'l Appl. . |
| 81/6186 | 9/1981 | South Africa . |
| 2137093 | 10/1984 | United Kingdom . |

OTHER PUBLICATIONS

Levinson; "The Defensive Role of Alkaloid, in Insects and Plants", *Experientia* 32, 408–411 (1976).
Wink, "Mollusk-Repellent Properties of . . . ", *Biol. Abstracts* 79, 16593 (1985).

*Primary Examiner*—Ferris H. Lander
*Attorney, Agent, or Firm*—Frederick H. Rabin

[57] ABSTRACT

An animal repellent composition comprising a first animal repellent component; a second component, which includes a synergistic amount of at least one alkaloid, and a carrier, wherein the first and second components do not occur together in nature. Compositions of the aforementioned type for use in molluscicide baits are also disclosed.

15 Claims, No Drawings

ANIMAL REPELLENT COMPOSITION AND METHOD

The present invention relates to animal control compositions and methods, and more particularly, it relates to animal repellent compositions and to methods for repelling animals.

It is frequently desired to exclude animals from certain areas, or to prevent or discourage animals from damaging such valuable objects as crops and the like. Whilst in an agricultural situation, such animals as rats, mice, wild dogs and the like may be excluded using appropriate fencing baits and traps, frequently in a domestic situation, such measures are extreme in that they may lead to the death or injury of animals. Naturally, the possibility of injury to an animal such as a domestic pet, would be viewed by the owner of such a pet to be unacceptable. Thus it is particularly difficult to discourage domestic pet from for example damaging small plants in a garden without providing an appropriate barrier around the plants. This is aesthetically undesirable in many instances and is not always sufficiently effective.

There also arises, particularly in domestic situations where substances toxic to domestic pets such as cats and dogs are applied to or around plants the probability that an animal will either come into contact with or consume such toxic substance. In most practical situations, contact with toxic substances does not frequently arise. However, the frequency of occurrence of dogs consuming in particular toxic molluscicides baits is quite high.

The present invention has particular application in this latter case. It is estimated that the incidence of dog poisoning by molluscicide baits in Australia is approximately of the order of 26 reported cases per veterinarian per year. Clearly, however, the real incidence of poisoning is probably much higher, since some cases would not be reported to a vet if for example the animal in question died before advice was sought.

In a paper by V. P. Studdert entitled "Epidemiological Features of Snail and Slug Bait Poisoning In Dogs and Cats" published in the Australian Veterinary Journal, 62 (8) 269–271. (1985), it is stated that the most commonly used preparations for such baits are "Bran-based powders, flakes, granules or pellets containing metaldehyde (metacetaldehyde) or methiocarb (3,5-dimethyl-4-methyl -mercaptophenyl-N-methyl-carbamate) for distribution on the ground". This paper further states that the products available in Australia are 2% methiocarb pellets and 1.5% metaldehyde powder or pellets. It is also noted in this paper that poisoning of dogs and cats by metaldehyde in such baits has been cited by others as an important cause of poisoning of animals in the United Kingdom, Canada and the U.S.

The present inventor also notes that in New Zealand Government legislation requires that an animal repellent be included in all metaldehyde based pellet baits.

As a consequence of the recognition of the incidence of poisoning with such baits, manufacturers of the baits in many countries here included substances to repel animals. Some of the substances used includes denatonium benzoate (a bittering agent), capsaicinoids (mucous membrane irritants) or various proprietary mixtures of essential oils. In addition, there are many other substances known in the art to have animal repellent properties.

In U.S. Pat. No. 3474176 (Freem) there are disclosed ketone based compositions in particular methyl nonyl ketone, which acts to repel cats, dogs and other warm blooded animals.

In other art there are disclosed many essential oil compositions exemplified by WO85/05009 (Dean et al) which discloses microencapsulated wormwood oil, ZA8106186 Nilse-Samson) which discloses a composition comprising lemon grass, orange oil, lemon oil, grapefruit oil, citronella, oil of bergamot and optionally oil of wintergreen and/or mustard oil, and US4320112 which discloses a mixture of napthalene and citronella in a plastics matrix. Numerous other types of compositions including compositions containing phenols, formaldehyde, ammonia and ammonium sulfide disclosed in EP113614 and compositions containing allyl or alkyl thiocyanates disclosed in GB2137093.

There is also disclosed in DE2738002 compositions containing a quinine alkaloid to protect trees from being eaten by wild animals.

As mentioned previously, the present inventor is aware of the use of many different compositions which have been used to repel domestic pets in particular from molluscicide type baits. However, the present inventor believes that there exists a need for alternate compositions to these known which would be more effective in their repellency and desirabily could be readily incorporated into baits and to have adequate duration of activity in use.

In experiments conducted to investigate the efficiency of some known repellent compounds, it was found that especially in the case of dogs of the hound variety, a potentially lethal dose of metaldehyde based pellets containing either denatonium benzoate or capsaicinoid would be consumed by a dog before the dog realised that the pellets were unpalatable. Further, the aforementioned repellents are extremely unpleasant to handle during manufacture of bait products.

Other compositions based on ketones, particularly those containing methylnonyl ketone show poor stability in use owing to their decomposition. In the presence of sunlight, their repellency lasts less than 24 hours. There is an added difficulty in such ketone compositions in that in pellet baits produced at high temperature and pressure, the volatility of the ketone results in its ineffective incorporation.

It has also been found that some essential oil compositions, whilst acting as a dog repellent, may also act to repel snails and slugs to the extent that the snails and slugs receive a sub-lethal dose of poison.

The present inventor has recognised these difficulties in the prior art compositions. In seeking to produce a composition that satisfied the criteria of an effective domestic pet repellent with stability in use, and ease of incorporation into bait products without being repellent to slugs and snails, the present inventor surprisingly discovered that when ipecacuanha extract was added to a known animal repellent, the resulting composition was considerably more effective as a domestic pet repellent than the known compositions alone. In effect, the present inventor has found that an ipecacuanha extract is able to synergise known animal repellent compositions.

The present invention consists in an animal repellent composition, comprising a first animal repellent component which includes at least one essential oil, a second component which includes at least one alkaloid, and a carrier, wherein the first and second components do not occur together in nature.

In a second aspect, the present invention consists in a method of repelling animals, which comprises exposing an animal to a repellent amount of a composition, the composition comprising a first animal repellent component an effective amount of a second component, which includes at least one alkaloid, and a carrier, wherein the first and second components do not occur together in nature.

It is preferred that the second component of the invention is ipecacuanha or an extract thereof. Ipecacuanha consists of the dried root or the rhyzome and root of *Cephaelis ipecacuanha* or *C. acuminata*. It contains the isoquinoline alkaloids emetine and cephaeline together with small proportions of psychotrine, methylpsychotrine and emetamine. Additionally, the root contains ipecacuanhic acid ipecacuanhin and starch.

Usually, Ipecacuanha is standardized in its powder form to contain about 2% of alkaloids calculated as emetine. When used in this form in the present composition, it is preferably present in an amount of 0.50% w/w, thereby providing a total alkaloid concentration in the composition of about 0.01% w/w as emetine.

When present in the form of an extract, it is usually an alcoholic extract containing about 8% w/w total alkaloids as emetine. Preferably, when used in the present invention, such an extract is present in the composition in an amount of 0.125% w/w thereby providing a total alkaloid concentration, as emetine, of about 0.01% w/w.

It is desirable, when the composition is in the form of a dry pellet or powder, that the aforementioned extract be absorbed onto a suitable base prior to incorporation into the composition, to produce a substantially dry, free flowing powder. The advantage of this step is that it enables the relatively small amount of ipecacuanha extract to be uniformly incorporated into the composition. A suitable type of base material is one selected from the group of compounds known as colloidal silicas, though there may be other materials known in the art which would also be acceptable.

The first component of the invention may be any animal repellent composition.

Preferably, the first component includes at least one of the essential oils, orange oil, terpinolene and geranium oil. Most preferably, the first component contains in addition to the aforementioned essential oils, at least one of diphenyl ether, cinnamaldehyde, methyl salicylate and diethyl phthalate. In this latter embodiment, preferably the concentration of the first component in the composition is 1% w/w.

In a third aspect, the present invention consists in a molluscicide bait composition, which is repellent to animals, comprising an effective molluscicide, a mollusc attractant, a first animal repellent component and a synergistic amount of a second component, which includes at least one alkaloid, wherein the first and second components do not occur together in nature.

Preferably, the molluscicide to which this aspect of the invention is directed are snails and slugs. In this embodiment the preferred molluscicide is metaldehyde or methiocarb. Though it will be realized that there are many other molluscicides known in the art which could be used in the present invention. It is also within the scope of this invention to employ a mixture of molluscicides.

If metaldehyde is used as the molluscicide, it is preferably included the composition in a concentration of not more than 10.0% w/w, most preferably in a concentration of 1.5% w/w.

If methiocarb is used as the molluscicide, it is preferably included in the composition in a concentration of not more than 5.0% w/w, most preferably in a concentration of 2.0% w/w.

Alternatively, a molluscicide selected from the group consisting of thiodicarb, mexacarbite and niclosamide could be used. Typically, the thiodicarb would be used in a concentration of about 2% w/w.

In order for a molluscicide bait composition to be effective, it is essential that the composition be attractive to the molluscs to be poisoned. Therefore, desirably, the components in the composition are selected to ensure that the composition is at least not repulsive to the molluscs before an attractant is added.

Preferably, the attractant is a starch based material, of which ground wheat is a suitable example. The attractant will generally form the majority of the composition on a weight basis since the concentration of the first and second component and the carrier is usually less than 20% w/w.

In this third aspect of the invention, the preferred first and second components are as for the first and second aspects of the present invention.

Compositions made according to the third aspect of the invention are particularly repellent towards dogs and cats. Therefore, the use of such compositions, should result in a substantial decrease in the number of animals poisoned.

Hereinafter by way of example only is a preferred embodiment of the present invention.

A dog and cat repellent molluscicide composition was made according to Formula IT shown below.

| Ingredient | Formula IT Concentration (% w/w) |
| --- | --- |
| Metaldehyde (active) | 1.5 |
| Green dye | 0.3 |
| Ground wheat (mollusc attractant) | 85.7 |
| Bentonite (binder) | 8.0 |

Sufficient ipecacuanha (second component) or ipecacuanha extract to provide a concentration of total alkaloids as emetine of 0.01%.

repellent 33523NR (obtained from Florasynth A/Asia Pty. Ltd.) 1.0% (first component).

Note that when ipecacuanha extract was used, it was absorbed onto Tixosil 38A (colloidal silica); Tixosil is the registered trade mark of Kofram and was used in a concentration of 3.0%.

The repellent first component comprised a mixture of essential oils and other substances.

The composition was formed into pellets under suitable pressure and temperature conditions.

In Formula IT, ground wheat was used as the attractant, whilst ipecacuanha or ipecacuanha extract formed the alkaloid containing second component. The animal repellent first component comprised the repellent 33523NR; the carrier being bentonite and where ipecacuanha extract was used, bentonite and Tixosil.

It should be noted that bentonite acts to bind the ingredients together and also to provide suitable weather resistance in use. That is, it acts to maintain the pellets in their original state.

In order to demonstrate the effectiveness of Formula IT in repelling cats and dogs and killing snails and slugs, a number of experiments were conducted as follows:

In experiment No. 1, a group of dogs were exposed in a controlled manner to firstly pellets made according to Formula IT with no alkaloid component (formula ITA), secondly to pellets made according to Formula IT with no first component (Formula ITB) and thirdly to pellets made according to Formula IT. The results are shown in Table I.

TABLE I

| Results of Experiment No. 1 | | | |
|---|---|---|---|
| | Formula ITA | Formula ITB | Formula IT |
| No. of Dogs Exposed | 29 | 12 | 13 |
| Result (No. of dogs that ate pellets) | 16 | 7 (plus one ate a third) | 0 (1 ate a little) |

In a second experiment, 11 of the dogs exposed to Formula ITB were now exposed to Formula IT and 13 of the dogs previously exposed to Formula IT were exposed to Formula ITB. The results of this experiment are shown in Table 2.

TABLE 2

| Results of Experiment No. 2 | | |
|---|---|---|
| | Formula ITB | Formula IT |
| No. of Dogs Exposed | 13 | 11 |
| Result (No. of dogs that ate pellets) | 9 plus two ate half each | 0 (3 nibbled a few pieces, and 1 dog salivated for a few minutes) |

If the results of the two experiments are combined, it can be seen that Formula ITA containing the first component only was consumed by 16 out of a group of 29 dogs; Formula ITB contains the second component only was consumed by 16 out of a group of 25 dogs and Formula IT containing both components was consumed by no dogs out of a group of 24 dogs.

It was further noted that whilst Formula ITB contained an effective amount of an emetic- namely ipecacuanha, in fact no emesis of the dogs occurred within one and a half hours of observation after ingestion and hence apomorphine had to be administered in order to induce emesis. It is thought that emesis did not occur because the dogs did not consume sufficient water.

In a separate experiment, designated R33, the effectiveness of a molluscicide animal repellant composition of the present invention was evaluated with dogs as follows:

A total of 10 dogs were used divided into two groups of five, each group being treated separately. All dogs were housed and fed under controlled conditions. Three different compositions were separately presented to each dog according to the following protocol:
1. Dogs offered normal food in one compartment of hopper and 100 g of composition in the other.
2. Dogs starved for 24 hours, then offered 100 g of composition and then fed.
3. Dogs starved for 48 hours, then offered 100 g of composition and then fed.
4. Dogs starved for 72 hours, then offered 100 g of composition and then fed.

The three compositions comprised -

A : formula IT with no metaldehyde, ipecacuanha or repellant essential oil blend.

B : formula IT with no metaldehyde and

C : formula IT.

The amount of composition remaining after exposure to a dog was weighed and the amount consumed determined. The results of this experiment is shown in table 3.

TABLE 3

| Results of Experiment R 33 Length of Starvation Mean Intake of Compositions (g) | | | | |
|---|---|---|---|---|
| Compositions | 0 Hours | 24 Hours | 48 hours | 72 hours |
| A | 0.6 | 30.1 | 44.4 | 53.3 |
| B | | | 0.1 | 7.4 |
| C | | 2.4 | 5.6 | 4.9 |

It can be seen from these results, that compositions Band C were consumed by dogs at a greatly reduced rate compared to composition A, which contained no repellant. Additionally, the presence of the molluscicide metaldehyde in composition C did not reduce the effectiveness of the repellent.

To confirm that Formula IT was still effective as a molluscicide, a series of experiment was conducted to compare the efficacy of Formula IT with Formula ITC (which contained no first or second component). The design of the experiments were as follows:

A replicated glasshouse trial was conducted on Lettuce and Petunia plants to evaluate the effectiveness of the formations IT an ITC. The control of the common garden snail (*Helix aspera*) and the garden slug (Deroceras. sp) under two watering patterns was evaluated. A single field trial was also conducted to confirm results obtained in the glasshouse.

The treatments evaluated in the glass house trial were:
1. Formula IT
2. Formula ITC
3. Untreated control All treatments were exposed to a simulated garden watering for 30 minutes (Mist) or remained dry (No Mist) after distribution of the pellets.

Three replicates of each bait treatment and each watering pattern was used for each of the two plant species, lettuce and petunias giving a total of 36 plots. Each plot consisted of one 200 mm plastic pot containing 3 plants of either Lettuce or Petunia in a sandy loam soil.

After the treatment and watering, four snails were placed in each plot in Replicates 1 and 2 and four slugs were replaced in Replicate 3 of each treatment. The pots were covered with nylon gauze to prevent the snails and slugs escaping. All pots were placed in trays to enable watering from beneath.

The plants were challenged with fresh snails and slugs again at 3, 7 and 14 days after treatment (DAT).

Assessments of plant damage and snail control were made at 1 and 3 days after the commencement of each challenge.

In the confirmatory field trial, a total of 100 snails were introduced to a garden bed (3m × 1m) containing lettuce seedlings. Seedlings were spaced 30 cm apart, the bed was 3 seedlings wide and 8 seedlings long. Nine piles of each bait were placed alternately and equidistant around the bed. Fifty snails were placed in 5 groups of 10 snails between the centre row of lettuce at the beginning of the trial and again 1 day later. Snails were assessed as active, knocked down or dead around each pile of pellets at 1 day, 3 days and 8 days after treatment.

It was found that Formula IT and ITC gave equal levels of snail and slug control in both the glasshouse and the field trial.

The simulated rainfall treatment had no significant effect on the performance of the formulation in controlling snails and slugs and in protecting plants from damage caused by snails and slugs.

Optimum snail and slug control was between the treatment time and 6 DAT. Snails and slugs were either knocked down or dead. Snail and slug control decreased from 8 DAT—17 DAT.

Both formulations gave equal protection to plants.

The results of the experiments 1 and 2 clearly demonstrate that the second component is able to synergise the first component and to thereby increase its repellent efficacy.

The results of the efficacy experiment shows that the molluscicide properties of compositions of the present invention are just as effective as compositions containing only active molluscicides.

I claim:

1. An animal repellent composition consisting essentially of (1) a first component which consists essentially of orange oil, terpinolene, diphenyl ether, geranium oil, diethyl phthalate, cinnamaldehyde and methyl salicylate, and (2) and a second component which is a sufficient quantity of ipecacuanha to provide an alkaloid concentration as emetine of about 0.01%.

2. A composition as in claim 1, wherein the ipecacuanha is included in the composition as an alcoholic extract containing about 8% w/w total alkaloids as emetine.

3. A composition as in claim 2, which additionally includes colloidal silica as a carrier.

4. A composition as claimed in claim 2, which is in the form of a free flowing powder.

5. A composition as claimed in claim 2, which is in the form of a pellet.

6. A molluscicide bait composition which is repellent to animals, said bait composition comprising an effective molluscicide, a mollusc attractant and an animal repellent composition consisting essentially of (1) a first component which consists essentially of orange oil, terpinolene, diphenyl ether, geranium oil, diethyl phthalate, cinnamaldehyde and methyl salicylate, and (2) a second component which is a sufficient quantity of ipecacuanha to provide an alkaloid concentration as emetine of about 0.01%.

7. A composition as in claim 6, wherein the ipecacuanha is included in the composition as an alcoholic extract containing about 8% w/w total alkaloids as emetine.

8. A composition as in claim 7, which is in the form of a powder or pellets.

9. A composition as in claim 6, wherein the molluscicide is a compound selected from the group consisting of metaldehyde, methiocarb, thiodicarb, mexacarbite and niclosamide.

10. A composition as in claim 9, wherein the concentration of metaldehyde in the composition is no more than 10% w/w.

11. A composition as in claim 9, wherein the concentration of metaldehyde in the composition is about 1.5% w/w.

12. A composition as in claim 9, wherein the concentration of methiocarb in the composition is no more than 5.0% w/w.

13. A composition as in claim 9, wherein the concentration of either methiocarb or thiodicarb is 2.0% w/w.

14. A composition as in claim 6, further comprising a starch-based material as an attractant.

15. A composition as in claim 14 wherein the starch-based material is ground wheat.

* * * * *